(12) United States Patent
Coffin

(10) Patent No.: US 7,063,835 B2
(45) Date of Patent: Jun. 20, 2006

(54) VIRUS STRAINS

(75) Inventor: Robert S. Coffin, London (GB)

(73) Assignee: Biovex Limited (GB)

( * ) Notice: Subject to any disclaimer, the term of this patent is extended or adjusted under 35 U.S.C. 154(b) by 0 days.

(21) Appl. No.: 10/181,692

(22) PCT Filed: Jan. 22, 2001

(86) PCT No.: PCT/GB01/00229

§ 371 (c)(1),
(2), (4) Date: Nov. 12, 2002

(87) PCT Pub. No.: WO01/53506

PCT Pub. Date: Jul. 26, 2001

(65) Prior Publication Data

US 2003/0113348 A1    Jun. 19, 2003

(30) Foreign Application Priority Data

| Jan. 21, 2000 | (GB) | .................................. 0001475.3 |
| Feb. 8, 2000 | (GB) | .................................. 0002854.8 |
| Jan. 5, 2001 | (GB) | .................................. 0100288.0 |
| Jan. 6, 2001 | (GB) | .................................. 0100430.8 |

(51) Int. Cl.
*A01N 63/00* (2006.01)
*A61K 48/00* (2006.01)
*A61K 39/12* (2006.01)
*A61K 39/245* (2006.01)
*C12N 7/00* (2006.01)

(52) U.S. Cl. ............... 424/93.2; 435/235.1; 424/199.1; 424/204.1; 424/205.1; 424/231.1; 424/93.1

(58) Field of Classification Search ............. 424/199.1, 424/204.1, 205.1, 229.1, 231.1, 93.1, 93.2, 424/93.6; 435/235.1, 236, 239, 320.1; 514/44; 536/23.7, 23.72
See application file for complete search history.

(56) References Cited

U.S. PATENT DOCUMENTS

| 5,328,688 A | 7/1994 | Roizman |
| 5,585,096 A | 12/1996 | Matuza et al. |
| 5,876,923 A | 3/1999 | Leopardi et al. |
| 6,428,968 B1 * | 8/2002 | Molnar-Kimber et al. . 435/7.23 |

FOREIGN PATENT DOCUMENTS

| WO | WO 92 13943 | 8/1992 |
| WO | WO 97 04804 | 2/1997 |
| WO | 97/20935 A | 6/1997 |
| WO | WO 97 26904 | 7/1997 |
| WO | 98/04726 A | 2/1998 |
| WO | 98/37905 A | 9/1998 |
| WO | 98/51809 A | 11/1998 |
| WO | WO 99/38955 | 8/1999 |
| WO | WO 00/08191 | 2/2000 |
| WO | 00/40734 A | 7/2000 |
| WO | WO 01/46449 | 6/2001 |
| WO | WO 01/46450 | 6/2001 |
| WO | WO 01/53505 | 7/2001 |
| WO | WO 01/53507 | 7/2001 |

OTHER PUBLICATIONS

Mullen et al., The Oncologist, vol. 7, pp. 106-119 (2002).*
Fulci et al., Frontiers in Bioscience vol. 8, pp. e346-360 (2003).*
Coukos et al., Cancer Gene Therapy, vol. 5, No. 6 (Supp), p. S7 (Nov. 1998).*
Toyoizumi et al., Cancer Gene Therapy, vol. 5 No. 6 (Supp), pp. S7-S8 (Nov. 1998).*
Goldsmith et al., Journal of Experimental Medicine, vol. 187 No. 3, pp. 341-358 (Feb. 1998).*
Bowie et al., Science, vol. 247 No. 4948, pp. 1306-1310 (Mar. 1990).*
Ace et al. (1989) "Construction and characterisation of a herpes simplex virus type 1 mutant unable to transinduce immediate early gene expression" J. Virology 63:2260-2269.
Chou et al. (1990) "Mapping of herpes simplex virus-1 neurovirulence to γ34.5, a gene nonessential for growth in culture" Science 250:1262-1266.
DeLuca et al. (1985) "Isolation and characterisation of deletion mutants of herpes simplex virus type 1 in the gene encoding immediate-early regulatory protein ICP4" J. Virology 56:558-570.
Gossen et al. (1995) "Transcriptional activation by tetracyclines in mammalian cells" Science 268:1766-1769.
Gossen & Bujard (1992) "Tight control of gene expression in mammalian cells by tetracycline-responsive promoters" Proc. Nat. Acad. Sci. USA 89-5547-5551.
Howard et al. (1998) "High efficiency gene transfer to the central nervous system of rodents and primates using herpes virus vectors lacking functional ICP27 and ICP34.5" Gene Therapy 5:1137-1147.
Hunter et al. (1999) "Attenuated replication-competent herpes simplex virus type 1 mutant G207:Safety evaluation of intracerebral injection in non-human primates" J. Virology 73:6319-6326.
Krisky et al. (1998) "Deletion of multiple immediate-early genes from herpes simplex virus reduces cytotoxicity and permits long-term gene expression in neurons" Gene Therapy 5:1593-1603.

(Continued)

Primary Examiner—James C. Housel
Assistant Examiner—Zachariah Lucas
(74) Attorney, Agent, or Firm—Fulbright & Jaworski L.L.P.

(57) ABSTRACT

The present invention relates to non-laboratory virus strains, for example of herpes viruses such as HSV, with improved oncolytic and/or gene delivery capabilities as compared to laboratory virus strains.

16 Claims, 3 Drawing Sheets

OTHER PUBLICATIONS

Maclean et al. (1991) "Herpeas simplex virus type 1 deletion variants 1714 and 1716 pinpoint neurovirulence-related sequences in Glasgow strain 17+ between immediate early gene 1 and the "a" sequence" J. Gen. virology 72:631-639.

MacFarlane et al. (1992) "Hexamethylene bisacetamide stimulates herpes simplex virus immediate early gene expressions in the absence of trans-induction by Vmw65" J. Gen. Virology 73:285-292.

Meignier et al. (1988) "In vivo behaviour of genetically engineered herpes simplex viruses R7017 and R7020: Construction and evaluation in rodents" J. Infect. Dis. 159:602-614.

Rice & Knipe (1990) "Genetic evidence for two distinct transactivation functions of the herpes simplex virus and protein ICP27" J. Virology 64:1704-1715.

Samaniego et al. (1995) "Functional interactions between herpes simplex virus immediate-early proteins during infection: Gene expression as a consequence of ICP27 and different domains of ICP4" J. Virology 69:5705-5715.

Samaniego et al. (1998) "Persistence and expression of the herpes simplex virus genome in the absence of immediate-early proteins" J. Virology 72:3307-3320.

Smiley & Duncan (1997) "Truncation of the C-terminal acidic transcriptional activation domain of herpes simplex virus VP16 Produces a phenotype similar to that of the in1814 linker insertion mutation" J. Virology 71:6191-6193.

Smith et al. (1992) "Evidence that the herpes simplex virus immediate early protein ICP27 acts post-transcriptionally during infection to regulate gene expression" Virology 186:74-86.

Thomas et al. (1999) "Herpes simplex virus latency associated transcript encodes a protein which greatly enhances virus growth, can compensate for deficiencies in immediate-early gene expression, and is likely to function during reactivation from virus latency" J. Virology 73:6618-6625.

Chambers et al; "Comparison of Genetically Engineered Herpes Simplex Viruses for the Treatment of Brain Tumors in a Mouse Model of Human Malignant Glioma"; Proceeding of the National Academy of Sciences of USA, vol. 92, No. 5, Feb. 28, 1995, pp. 1411-1415, XP002090032.

Andreansky et al. (1997); "Evaluation of genetically engineered herpes simplex viruses a oncolytic agents for human malignant brain tumors" Cancer Res. 57(8): 1502-1509.

Ejercito et al. (1968); "Characterisation of herpes simplex virus strains differing in their effects on social behaviour of infected cells." J. Gen. Virol. 2: 357-364.

Krisky et al. (1998); "Development of herpes simplex virus replication-defective multigene vectors for combination gene therapy applications" Gene Therapy 5(11): 1517-1530.

Lachmann & Efstathiou (1999); "Gene transfer with herpes simplex vectors" Curr. Opin. Mol. Ther. 1(5): 622-632.

Moriuchi et al. (1998); "Enhanced tumor cell killing in the presence of ganciclovir by herpes simplex virus type 1 vector-directed coexpression of human tumor necrosis factor-alpha and herpes simplex thymidine kinase" Cancer Res. 58(24): 5731-5737.

Randazzo et al. (1996) "Herpes simplex 1716 an ICP 34.5 mutant is severely replication restricted in human skin xenografts in vivo" Virology 223(2): 392-395.

Speck et al. (1996); "The application of genetically engineered herpes simplex viruses to the treatment of experimental brain tumors" J. Gen. Virol. 77(10): 2563-2568.

Andreansky et al, "The Application of Genetically Engineered Herpes Simplex Viruses to the Treatment of Experimental Brain Tumors," Proc. Natl. Acad. Sci. vol. 93, pp. 11313-11318 (Oct. 1996).

Chou et al, "The γ134.5 Gene of Herpes Simplex Virus 1 Precludes Neuroblastoma Cells from Triggering Total Shutoff of Protein Synthesis Characteristic of Programmed cell Death in Neuronal Cells," Proc. Natl. Acad. Sci. vol. 89, pp. 3266-3270 (Apr. 1992).

Chou et al, "Differential response of Human Cells to Deletions and Stop Condons in the Y134.5 Gene of Herpes Simplex virus," Journal of Virology, pp. 8304-8311 (Dec. 1994).

Coukos et al, "Oncolytic Herpes Simplex Virus-1 Lacking ICP34.5 Induces p53-independent Death and Is Efficacious against Chemotherapy-resistant Ovarian Cancer," Clinical Cancer Research vol. 6, pp. 3342-3353 (Aug. 2000).

Ezzeddine et al, "Selective Killing of Glioma Cells in Culture and in Vivo by Retrovirus Transfer of the Herpes Simplex Virus Thymidine Kinase Gene," The New Biologist vol. 3, No. 6, pp. 608-614 (Jun. 1991).

Markert, James et al, "Reduction and Elimination of Encephalitis in an Experimental Glioma Therapy Model with attenuated Herpes Simplex Mutants that Retain Susceptibility to Acyclovir," Neurosurgery vol. 32 No. 4, pp. 597-603.

Martuza et al, "Experimental Therapy of Human Glioma by Means of a Genetically Engineered Virus Mutant," Science vol. 252, pp. 854-856.

McKie et al, "Selective in Vitro Replication of Herpes Simplex Virus 1 (HSV-1) ICP34.5 Null Mutants in Primary Human CNS Tumours—Evaluation of a Potentially Effective Clinical Therapy," British Journal of Cancer vol. 74, pp. 745-752 (1996).

Liu, B.L., et al.; ICP34.5 deleted herpes simplex virus with enhanced oncolytic, immune stimulating, and anti-tumour properties (Research Article); Gene Therapy (2003) 10, 292-303.

U.S. Appl. No. 10/181,697, filed Nov. 12, 2002.

Rekabdar, Elham, et al.; Variablility of the Glycoprotein G. Gene in Clinical Isolates of Herpes Simplex Virus Type 1; Clinical and Diagnostic Laboratory Immunology, vol. 6 (6): 826-831, Nov. 1999.

Shi, Fu-Shun, et al.; Granulocyte-macrophage colony-stimulating factor (GM-CSF) secreted by cDNA-transfected tumor cells induces a ore potent antitumor response than exogenous GM-CSF; Cancer Gene Therapy, vol. 6 (1);81-88, 1999.

Irvine, Kari R., et al.; Cytokine Enhancement of DNA Immunization Leads to Effective Treatment of established Pulmonary Metastases; The Journal of Immunology, 156:238-245, 1996.

Bronte, Vincenzo, et al.; IL-2 Enhances the Function of Recombinant Poxvirus-Based Vaccines in the Treatment of Established Pulmonary Metastases; The Journal of Immunology, 154-5282-5292, 1995.

Andreansky, S., et al.; Treatmentof intracranial gliomas in immunocompetent mice using herpex simplex viruses that express murine interleukins; Gene Therapy, 5:121-130, 1998.

* cited by examiner

VIRUS STRAINS

This application is the US national phase of international application PCT/GB01/00229 filed Jan. 22, 2001, which designated the US and was published in English.

FIELD OF THE INVENTION

The present invention relates to non-laboratory virus strains, for example of herpes viruses such as HSV, with improved oncolytic and/or gene delivery capabilities as compared to laboratory virus strains.

BACKGROUND OF THE INVENTION

Viruses have been suggested or demonstrated to have utility in a variety of applications in biotechnology and medicine on many occasions. Each is due to the unique ability of viruses to enter cells at high efficiency. This is followed in such applications by either virus gene expression and replication and/or expression of an inserted heterologous gene. Thus viruses can either deliver and express genes in cells (either viral or other genes) which may be useful in for example gene therapy or the development of vaccines, or they may be useful in selectively killing cells by lytic replication or the action of a delivered gene in for example cancer.

Herpes simplex virus (HSV) has been suggested to be of use both as a gene delivery vector in the nervous system and elsewhere and for the oncolytic treatment of cancer. In both applications the virus must however be disabled such that it is no longer pathogenic but such that it can still enter cells and perform the desired function. Thus for non-toxic gene delivery to target cells using HSV it has become apparent that in most cases immediate early gene expression must be prevented/minimised from the virus. For the oncolytic treatment of cancer, which may also include the delivery of gene(s) enhancing the therapeutic effect, a number of mutations to HSV have been identified which still allow the virus to replicate in culture or in actively dividing cells in vivo (e.g. in tumours), but which prevent significant replication in normal tissue. Such mutations include disruption of the genes encoding ICP34.5, ICP6 and thymidine kinase. Of these, viruses with mutations to ICP34.5, or ICP34.5 together with mutations of e.g. ICP6 have so far shown the most favourable safety profile. Viruses deleted for only ICP34.5 have been shown to replicate in many tumour cell types in vitro and to selectively replicate in artificially induced brain tumours in mice while sparing surrounding tissue. Early stage clinical trials have also shown their safety in man.

However, while promise has been shown for various viruses including HSV for gene delivery/therapy or for the oncolytic treatment of cancer, the majority of this work has used virus strains which have been maintained in tissue culture cells for many years. In applications where the virus merely needs enter cells to deliver genes this may not prove problematical as maintenance in cell culture also requires the virus to enter cells, albeit often cells of a different type or species in comparison to the likely target cells for a vector. However, in applications where other properties are required, the use of laboratory virus strains may not allow the full potential of a virus in a particular application to be utilised.

HSV has the unique ability amongst viruses currently under development as vectors in that it has naturally evolved to infect and remain latent in neurons. HSV has also evolved to be highly efficiently transported along nerves from the site of infection, usually at the periphery, to the neuronal cell body, usually in the spinal ganglia. Such capabilities are not required in cell culture and as such capabilities require specific evolved properties of HSV, further adaption to growth in culture may have resulted in optimally efficient axonal transport capabilities to have been lost. HSV vectors for gene delivery to the central or peripheral nervous system are likely to show maximum effectiveness if axonal transport properties have been retained at maximum efficiency. Here, inoculation at a peripheral site would then allow maximally efficient gene delivery to peripheral neuron cell bodies, and inoculation in the brain would allow maximally efficient gene delivery to multiple connected sites. Current vectors based on laboratory strains of HSV may not allow this to occur at the maximum efficiency possible. Indeed, because of HSV's high capacity to be transported along nerves, there is potentially a particularly large discrepancy between the properties which it is desired to conserve and those likely to be retained in culture.

HSV and other viruses such as adeno- or rheovirus also have potential utility in the oncolytic treatment of cancer. However, again viruses under development for such purposes have previously been extensively maintained in culture. As the oncolytic treatment of cancer requires active replication in often relatively slowly growing human tumour cells, it would be anticipated that adaptation of laboratory virus strains to growth in particular cultured cells may have reduced the efficiency with which such lytic replication in human tumour cells, or infection of human tumour cells, could optimally occur.

SUMMARY OF THE INVENTION

The present invention provides the opportunity to develop viruses with improved in vivo capabilities of gene transfer and/or lytic destruction of tumour cells. Here, virus strains are constructed appropriate for these purposes based on recent clinical isolates of the appropriate virus rather than the serially passaged laboratory strains which have previously been used. The present invention therefore has the potential to provide viruses with improved capabilities of infecting human cells in vivo, improved replicative/lytic capability in such cells, and (in the case of HSV) improved abilities of trafficking along nerves from the inoculation site to the neuronal cell body. The invention is exemplified using HSV but is equally applicable for other viruses currently under development as vectors and/or for the oncolytic destruction of cancer cells.

We have shown that two clinical isolates of HSV1 (strains JS1 and BL1) have enhanced replication in some human tumour cell lines as compared to HSV1 strain 17+ (a standard laboratory strain).

We have deleted ICP34.5 from the clinical isolate JS1 strain and again compared replicative potential in human tumour cell types in comparison to HSV1 strain 17+ (a standard laboratory strain) in which ICP34.5 was also deleted. This strain (JS1/ICP34.5−) is a modified strain derived from a clinical isolate, and is thus a modified non-laboratory strain of the invention.

JS1 with ICP34.5 deleted showed enhanced growth in some human tumour cells tested as compared to HSV1 ICP34.5 deleted strain 17+, i.e. a laboratory strain virus with the same modification. However, as compared to the laboratory strain derived from strain 17+, cell killing capabilities were enhanced with the JS1/ICP34.5− virus in all tumour cell lines tested.

Thus, the use of non-laboratory virus strains can be seen to enhance the anti-tumour capabilities of such viruses and was evident in all the tumour cell lines tested so far. This will have applicability for cancer treatment in human patients.

Further enhanced activity may also be anticipated if these viruses are then used to deliver genes with anti-tumour activity. Such genes include those encoding pro-drug activators, tumour suppressor or pro-apoptotic factors, or immune stimulatory proteins.

For this purpose, we have produced an ICP34.5 deleted clinical isolate of HSV1 which expresses human GMCSF. This virus is designed to enhance anti-tumour immune responses following intra-tumoral injection.

The invention also provides viruses of the invention which carry a heterologous gene/genes. The term heterologous gene is intended to embrace any gene not found in the viral genome. The heterologous gene may be any allelic variant of a wild-type gene, or it may be a mutant gene. Heterologous genes are preferably operably linked to a control sequence permitting expression of said heterologous gene in a cell in vivo. Viruses of the invention may thus be used to deliver a heterologous gene/genes to a cell in vivo where it will be expressed. For oncolytic virus therapy, such genes typically encode proteins capable of enhancing the tumour destroying properties of the virus. These genes may encode proteins which are themselves cytotoxic, are pro-drug activating, or which may be capable of stimulating/enhancing an anti-tumour immune response. For gene delivery to the peripheral nervous system using HSV, the heterologous gene/genes may encode a polypeptide capable of modifying responses to painful stimuli or reducing chronic pain, for example a protein capable sequestering e.g. nerve growth factor, other pain modulating neurotrophic factor or neurotrophic factor-like molecules, or substance P or other neuropeptides. The heterologous gene/genes may also encode a polypeptide capable of stimulating the re-growth of damage nerves or preventing the further degeneration of nerves in degenerative conditions. In the central nervous system, heterologous genes may include those potentially beneficial in neurodegenerative disease such as Parkinson's disease or Alzheimer's disease and might typically include genes encoding neurotrophic factors and/or enzymes capable of enhancing the activity of remaining cells in such diseases. In all cases, single or multiple heterologous genes may be carried by a single virus.

Accordingly the invention provides:

Use of a modified, oncolytic, non-laboratory virus strain in the manufacture of a medicament for the oncolytic treatment of cancer;

Use of a modified, replication incompetent, non-laboratory virus strain comprising a heterologous gene in the manufacture of a medicament for the delivery of said gene to a subject;

A method of determining whether a gene has an effect on a phenotype associated with a peripheral nervous system disorder or on a cell of the peripheral nervous system which is relevant to a peripheral nervous system disorder, which method comprises:
  (i) inoculating a replication incompetent herpes virus of the invention comprising a heterologous gene into a peripheral nerve; and
  (ii) monitoring a phenotype of said disorder or an effect of expression of said gene on said cell to determine thereby whether said gene has an effect relevant to said disorder;

A method of determining whether a gene has an effect on a phenotype associated with a central nervous system disorder or on a cell of the central nervous system which is relevant to a central nervous system disorder, which method comprises:
  (i) inoculating into a cell of the central nervous system with a replication incompetent herpes virus of the invention; and
  (ii) monitoring a phenotype of said disorder or an effect of expression of said gene on said cell to determine thereby whether said gene has an effect on said cell or said phenotype;

A method of determining whether a gene encodes an antigen associated with a pathogenic infection or cancer, which method comprises infecting a dendritic cell or a macrophage with a replication incompetent virus of the invention comprising a heterologous gene encoding an antigen and monitoring antigen presentation of the polypeptide product of said gene, or an effect of expression of said gene, or a phenotype of said pathogenic infection or cancer to determine thereby whether said gene encodes an antigen associated with said infection or cancer and which itself has therapeutic potential or is a target for therapeutic intervention;

A method of determining the suitability of a non-laboratory virus strain for modification into a modified strain as defined herein, comprising:
  (i) optionally, isolating a non-laboratory virus strain from a host;
  (ii) providing said non-laboratory virus strain;
  (iii) assessing the properties of the virus in respect of one or more desirable characteristics; and, optionally,
  (iv) selecting for modification virus strains with desirable properties;

A method of determining the suitability of a non-laboratory virus strain for modification into a modified oncolytic strain of the invention, comprising:
  (i) optionally, isolating a non-laboratory virus strain from a host;
  (ii) assessing the growth of the virus in one or more types of tumour cell; and optionally
  (iii) selecting for modification virus strains with a high growth rate or cell killing capability;

A method of determining the suitability of a non-laboratory virus strain for modification into a modified oncolytic strain, comprising:
  (i) providing a non-laboratory virus strain, optionally one selected by a method as just defined;
  (ii) modifying said strain such that it becomes oncolytic; and
  (iii) assessing the ability of said modified, oncolytic non-laboratory strain to kill tumour cells; and optionally
  (iv) selecting strains that exhibit high tumour cell-killing capacity for further modifications; and optionally
  (v) carrying out further modifications;

A method of determining whether a gene enhances the anti-tumour effects of a virus comprising:
  (i) providing a modified, oncolytic non-laboratory strain of the invention;
  (ii) inserting said gene into said virus as a heterologous gene; and
  (iii) assessing the ability of said modified, oncolytic non-laboratory strain to kill tumour cells compared to the ability of the precursor strai=n provided in step (i);

A method of producing a modified, oncolytic, non-laboratory virus strain comprising:
  (i) isolating from a host a non-laboratory strain of a virus;
  (ii) optionally determining its suitability for modification as defined above; and
  (iii) modifying it to render it oncolytic, and optionally
  (iv) carrying out further modifications;
A method of producing a modified non-laboratory virus strain comprising:
  (i) providing a non-laboratory strain of a virus;
  (ii) modifying it to render it replication incompetent and,
  (iii) inserting a heterologous gene;
A modified, oncolytic, non-laboratory virus strain as defined herein;
A modified non-laboratory virus strain comprising a heterologous gene, as defined herein
Use of a gene identified as having an effect on a phenotype associated with a peripheral nervous system disorder or on a cell of the peripheral nervous system which is relevant to a peripheral nervous system disorder by a method as defined above, or of a gene product encoded by said gene in the manufacture of a medicament for the treatment of a peripheral nervous system disorder;
Use of a gene identified as having an effect on a phenotype associated with a central nervous system disorder or on a cell of the central nervous system which is relevant to a central nervous system disorder by a method as defined above, or of a gene product encoded by said gene in the manufacture of a medicament for the treatment of a central nervous system disorder;
Use of a gene identified as encoding an antigen associated with a pathogenic infection or cancer by a method as defined above, or of an antigen encoded by said gene in the manufacture of a medicament for the treatment or prevention of said infection or cancer;
A non-laboratory virus strain identified by, or produced in the course of, a method of the invention;
Use of a gene identified as enhancing the anti-tumour effects of a virus by a method as defined above, or of a gene product encoded by said gene, in the manufacture of a medicament for the treatment or prevention of cancer;
A modified non-laboratory virus strain obtained or obtainable by a method of the invention;
HSV1 strain JS1 as deposited at the European Collection of Cell Cultures (ECACC) under accession number 01010209, or an HSV1 strain derived therefrom, a pharmaceutical composition comprising such a virus; such a virus for use in the treatment of the human or animal body.
A method of treating a tumour in an individual in need thereof by administering to said individual an effective amount of an oncolytic virus of the invention;
A method of delivering a gene to an individual in need thereof by administering to said individual an effective amount of a non-oncolytic virus of the invention; and
A method of treating or preventing a central peripheral nervous system disorder by administering to a peripheral nerve of an individual in need thereof an effective amount of a neurotrophic virus of the invention.

DETAILED DESCRIPTION OF THE INVENTION

A. Viruses

Virus Strains of the Invention

Figure 1:
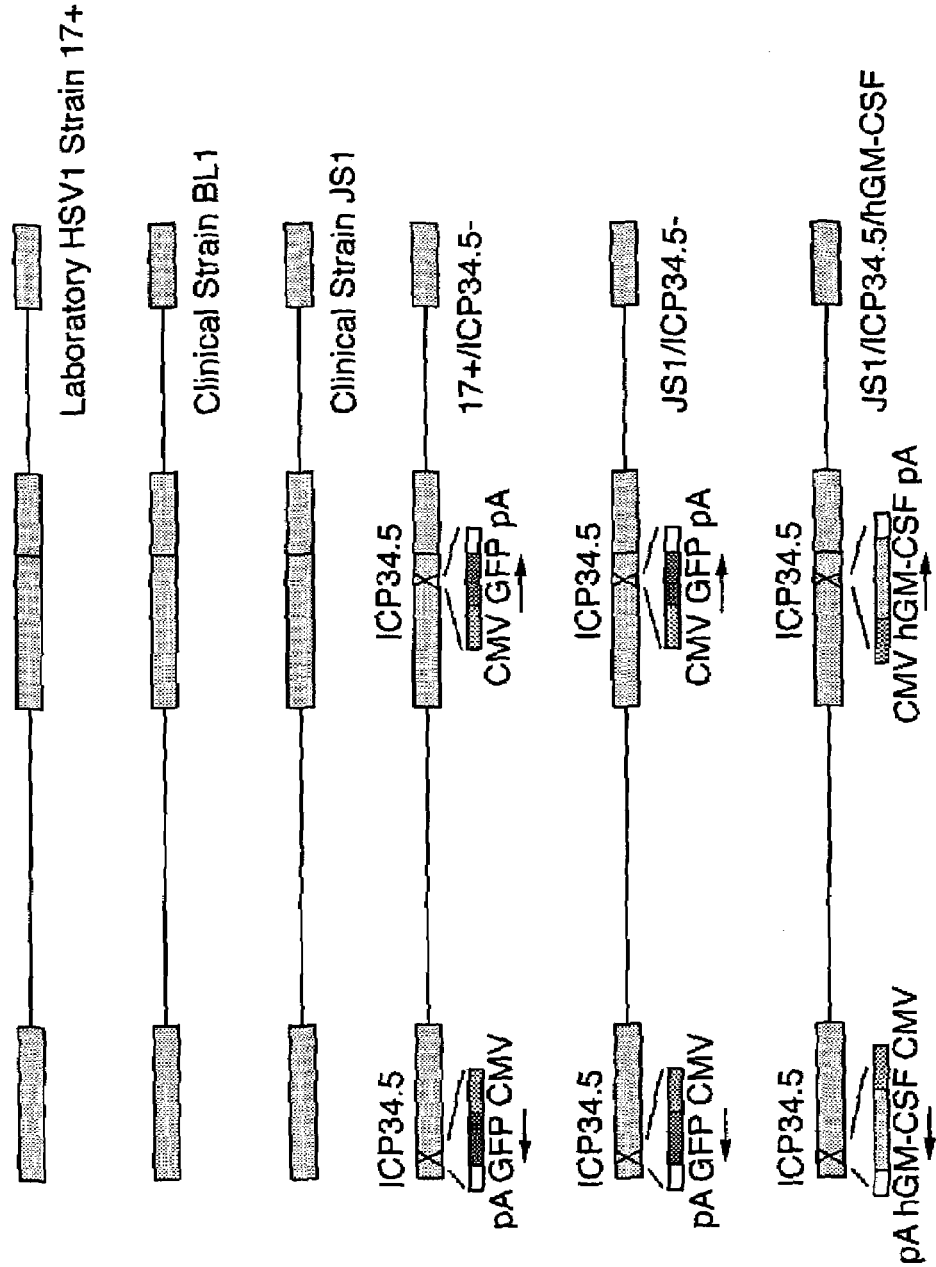
FIG. 1. Viruses
From top to bottom, diagrams show: laboratory HSV1 strain 17+, clinical strain BL1, clinical strain JS1, 17+/ICP34.5−, JS1 /ICP34.5−, JS1/ICP34.5−/ICP47−/hGMCSF.

The invention is applicable to viruses in general. Preferably, a virus strain of the invention will be a strain of a herpes virus, adenovirus, picomavirus, retrovirus or alphavirus. More preferably, a virus strain of the invention will be a strain of a herpes virus. Still more preferably, a virus strain of the invention will be a strain of a herpes simplex virus (HSV), typically a strain of HSV1 or HSV2.

When the virus of the invention is a herpes simplex virus, the virus may be derived from, for example HSV1 or HSV2 strains, or derivatives thereof, preferably HSV1. Derivatives include inter-type recombinants containing DNA from HSV1 and HSV2 strains. Such inter-type recombinants are described in the art, for example in Thompson et al (1998) and Meignier et al (1988). Derivatives preferably have at least 70% sequence homology to either the HSV1 or HSV2 genomes, more preferably at least 80%, even more preferably at least 90 or 95%. More preferably, a derivative has at least 70% sequence identity to either the HSV1 or HSV2 genome, more preferably at least 80% identity, even more preferably at least 90%, 95% or 98% identity.

For example the UWGCG Package provides the BEST-FIT program which can be used to calculate homology (for example used on its default settings) (Devereux et al. (1984) *Nucleic Acids Research* 12, p387–395). The PILEUP and BLAST algorithms can be used to calculate homology or line up sequences (typically on their default settings), for example as described in Altschul (1993) J. Mol. Evol. 36:290–300; Altschul et al. (1990) J. Mol. Biol. 215:403–10.

Software for performing BLAST analyses is publicly available through the National Centre for Biotechnology Information's website. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

Properties of Virus Strain of the Invention

Virus strains of the invention are "non-laboratory" strains. They can also be referred to as "clinical" strains. A person of skill in the art will readily be able to distinguish between a laboratory strain and a non-laboratory, or clinical, one. Further guidance on the properties likely to be exhibited by virus strains is given below.

The key distinction between a laboratory and non-laboratory strain is that laboratory strains currently in common use have been maintained for long periods, many years in some cases, in culture. The culture of viruses such as HSV involves a technique known as serial passage. To grow and maintain viruses, suitable cells are infected with the virus, the virus replicates within the cell and the virus is then harvested; fresh cells are then re-infected. this process constitutes one cycle of serial passage. Each such cycle may take, for example, a few days in the case of HSV. As discussed above, such serial passaging may lead to changes in the properties of the virus strain, in that selection takes places for properties that favour growth in culture (e.g. rapid replication), as opposed to properties useful for practical applications, e.g. maintenance of the capacity to travel along axons in the case of HSV.

Virus strains of the invention are non-laboratory strains in that they are derived from strains recently isolated from infected individuals. Strains of the invention are modified compared to the original clinical isolates, and may have spent a time in culture, but any time spent in culture will be comparatively short. Strains of the invention are prepared in such a manner as to retain substantially the desirable properties of the original clinical isolates from which they are derived.

A virus of the invention is capable of efficiently infecting target human cells. Such a virus is recently isolated from an infected individual and then screened for the desired ability of enhanced replication in tumour and/or other cells in vitro and/or in vivo in comparison to standard laboratory strains, or (in the case of neurotrophic viruses such as HSV) for an enhanced ability to traffic along nerves as compared to standard laboratory strains using an in vivo model. Such viruses with improved properties as compared to laboratory virus strains are viruses of the invention. Identified viruses with such desired improved properties can then be engineered such that they can selectively kill tumour cells by the mutation of appropriate gene(s), or mutated such that they can deliver a gene(s) to target tissue without toxic effect in non-oncolytic applications. These modified viruses are also viruses of the invention. Alternatively, virus strains may be isolated from an infected individual and mutations anticipated to be appropriate for oncolytic therapy and/or gene delivery made. These modified viruses are then screened for the desired improved properties as compared to laboratory strains, viruses with such improved properties providing further viruses of the invention.

Further guidance on the likely properties of the virus strains of the invention is provided as follows.

Preferably, a virus strain of the invention has undergone three years or less in culture since isolation of its unmodified clinical precursor strain from its host. More preferably, a strain of the invention has undergone one year or less in culture, for example nine months or less, six months or less, three months or less, or two months or less, one month or less, two weeks or less, or one week or less. By these definitions of time in culture, is meant time actually spent in culture. Thus, for example, it is a common practice to freeze virus strains in order to preserve them. Evidently, preserving by freezing or in an equivalent manner does not qualify as maintaining the strain in culture. Thus, time spent frozen or otherwise preserved is not included in the above definitions of time spent in culture. Time spent in culture is typically time actually spent undergoing serial passage, i.e. time during which selection for undesirable characteristics can occur.

Preferably, a virus strain of the invention has undergone 1,000 or less cycles of serial passage since isolation of its unmodified clinical precursor strain from its host. More preferably, it has undergone 500 or less, 100 or less, 90 or less, 80 or less, 70 or less, 60 or less, 50 or less, 40 or less, 30 or less, 20 or less, or 10 or less such cycles.

Preferably, a virus of the invention has a greater ability, as measured by standard statistical tests, than a reference laboratory strain with the equivalent modifications to perform certain functions useful in the application at hand. For example, in the case of an oncolytic virus for tumour treatment, a virus strain of the invention will preferably have a greater ability than a reference laboratory strain with equivalent modifications to infect or replicate any tumour cell, to kill tumour cells or to spread between cells in tissue. More preferably, such greater ability is a statistically significantly greater ability. For example, according to the invention, a may have up to 1.1 fold, 1.2 fold, 1.5 fold, 2 fold, 5 fold, 10 fold, 20 fold, 50 fold, or 100 fold the capacity of the reference strain in respect of the property being tested.

Preferably, a virus of the invention has, i.e. retains, substantially the ability of its unmodified clinical precursor strain in respect of one or more of the properties characteristic of usefulness in the application at hand. For example, in the case of an oncolytic virus intended for the treatment of tumours, a virus strain of the invention preferably has substantially the ability of its unmodified clinical precursor strain to infect or replicate a tumour cell, kill tumour cells or to spread between cells in tissue.

Preferably, according to the invention, a virus retains substantially the properties of its unmodified clinical precursor strain if, in a quantitative test, it retains 75%, more preferably 80, 90, 95, 98, 99 or 100% of the capacity of the unmodified clinical precursor strain in respect of the property being tested. More preferably, in respect of the property being tested, any differences between the unmodified clinical precursor strain and the modified strain of the invention will not be statistically significant.

Statistical analysis of the properties described herein may be carried out by standard tests, for example, t-tests, ANOVA, or Chi squared tests. Typically, statistical significance will be measured to a level of p=0.05 (5%), more preferably p=0.01, p=0.001, p=0.0001, p=0.000001.

Modifications

Viruses of the invention are typically modified as compared to their precursor clinical strains. In particular, certain genes will typically be rendered non-functional, and the viruses may also comprise a heterologous gene(s). Typically, viruses of the invention are attenuated.

Viral regions altered for the purposes described herein may be either eliminated (completely or partly), or made non-functional, or substituted by other sequences, in particular by a heterologous gene sequence. One or more genes may be rendered non-functional, and one or more heterologous genes inserted.

Oncolytic Viruses of the Invention

In one embodiment, viruses of the invention are modified, oncolytic, non-laboratory viruses. These will be useful in the oncolytic treatment of cancer. Such viruses infect and replicate in tumour cells, subsequently killing the tumour cells. Thus, such viruses are replication competent. Preferably, they are selectively replication competent in tumour cells. This means that either they replicate in tumour cells and not in non-tumour cells, or that they replicate more effectively in tumour cells than in non-tumour cells. Measurement of selective replication competence can be carried out by the tests described herein for measurement of replication and tumour cell-killing capacity, and also analysed by the statistical techniques mentioned herein if desired.

An oncolytic virus of the invention preferably has a greater ability than a reference laboratory strain with the same modifications to infect or replicate in a tumour cell, to kill tumour cells or to spread between cells in tissues. Preferably, this ability is a statistically significantly greater ability as described herein. The properties of the virus strain in respect of tumour cells can be measured in any manner known in the art.

For example, the capacity of a virus to infect a tumour cell can be quantified by measuring the dose of virus required to measure a given percentage of cells, for example 50% or 80% of cells. The capacity to replicate in a tumour cell can be measured by growth measurements such as those carried out in the Examples (see FIG. 2), e.g. by measuring virus growth in cells over a period of 6, 12, 24, 36, 48 or 72 hours or longer.

The ability of a virus to kill tumour cells can be roughly quantitated by eye (see FIG. 3) or more exactly quantitated by counting the number of live cells that remain over time for a given time point and MOI for given cell type. For example, comparisons may be made over 24, 48 or 72 hours and using any known tumour cell type. In particular, HT29 colorectal adenocarcinoma, LNCaP.FGC prostate adenocarcinoma, MDA-MB-231 breast adenocarcinoma, SK-MEL-28 malignant melanoma or U-87 MG glioblastoma astrocytoma cells can be used. Any one of these cell types or any combination of these cell types can be used, as may other tumour cell types. It may be desirable to construct a standard panel of tumour cell types for this purpose. To count the number of live cells remaining at a given time point, the number of trypan blue-excluding cells (i.e. live cells) can be counted. Quantitation may also be carried out by fluorescence activated cell sorting (FACS) or MTT assay. Tumour cell-killing ability may also be measured in vivo, e.g. by measuring the reduction in tumour volume engendered by a particular virus.

The ability of a virus to spread in tissue, especially solid tissue, can be measured by determining the number of cells at sites connected to the site of the original infection.

In order to determine the properties of viruses of the invention, it will generally be desirable to use a standard laboratory reference strain for comparison. Any suitable standard laboratory reference strain may be used. In the case of HSV, it is preferred to use one or more of HSV1 strain 17+, HSV1 strain F or HSV1 strain KOS. The reference strain will typically have equivalent modifications to the strain of the invention being tested. Thus, the reference strain will typically have equivalent modifications, such as gene deletions and/or heterologous gene insertions. For example, in the case of an HSV strain, if the ICP34.5 and ICP47-encoding genes have been rendered non-functional in the virus of the invention, then they will also be rendered non-functional in the reference strain. The modifications made to the reference strain may be identical to those made to the strain of the invention. By this, it is meant that the gene disruptions in the reference strain will be in exactly equivalent positions to those in the strain of the invention, e.g. deletions will be of the same size and in the same place. Similarly, in these embodiments, heterologous genes will be inserted in the same place, driven by the same promoter, etc. However, it is not essential that identical modifications be made. What is important is that the reference gene has functionally equivalent modifications, e.g. that the same genes are rendered non-functional and/or the same heterologous gene or genes is inserted.

In an oncolytic virus of the invention, suitable modifications will be made to the virus to confer oncolytic activity, if it is not naturally present, and preferably to confer selective oncolytic activity.

In the case of HSV, such mutations allowing selective oncolytic activity include mutation to the genes encoding ICP34.5, ICP6 and/or thymidine kinase (TK), preferably ICP34.5. Such mutations to the ICP34.5-encoding gene in laboratory strains of HSV are described in Chou et al 1990, Maclean et al 1991, although any mutation in which ICP34.5 is non-functional may be used.

Accordingly, in an HSV strain, the viruses preferably modified such that it lacks one or more of a functional ICP34.5-encoding gene, a functional ICP6-encoding gene, a functional glycoprotein H-encoding gene, a functional thymidine kinase-encoding gene; or in a non-HSV strain, the virus lacks a functional gene equivalent to one of said HSV genes.

More preferably, the virus lacks a functional ICP34.5-encoding gene.

Other modifications may also be made. In particular, in the case of HSV, the virus may be modified such that it lacks a functional ICP47 gene. This is because ICP47 usually functions to block antigen presentation in HSV-infected cells so its disruption leads to a virus that does not confer on infected tumour cells particular properties that might protect such HSV infected cells from the host's immune system.

Viruses with any other genes deleted/mutated which provide oncolytic properties (ie selective replication in tumours compared to surrounding tissue) are also viruses of the invention as those skilled in the art will recognise that the above list is not exhaustive and identification of the function of other genes in any of the viruses above may suggest the construction of new viruses which are also viruses of the invention.

Heterologous gene(s) may also be inserted into such viruses of the invention by techniques known in the art and/or described herein. In an oncolytic virus, the heterologous gene will typically be one that enhances the capacity of the virus to counteract tumours. Any genes conferring on the virus anti-tumour properties may thus be inserted. In particular, the heterologous gene may be a gene capable of modifying immune response to the tumour cells in a beneficial manner, especially an immune stimulatory polypeptide such as CD40L, granulocyte macrophage-colony-stimulating factor (GMCSF), another cytokine or chemokine (e.g.RANTES), B7.1 or B7.2 or IL12. Alternatively, the heterologous gene may encode a pro-drug activator, such as nitroreductase or cytochrome P450. In this context, combined treatment of tumours with the pro-drug activated by the pro-drug activator and a virus of the invention is envisaged. Alternatively, the heterologous gene may encode a tumour suppressor, such as p53.

Other Virus Strains of the Invention

In other embodiments, non-oncolytic viruses are desirable. These may be replication incompetent viruses. Their function is typically to deliver heterologous genes to an individual.

In particular, for use as a vector in non-oncolytic applications, mutations may be made such that virus regulatory immediate early gene expression is minimised. Thus, the genes encoding ICP4, ICP27, ICP22 and/or ICP0 may be inactivated or deleted either individually or in combination, or mutations in the virion trans-activator protein vmw65 included preventing/reducing its trans-activating ability. In particularly preferred embodiments for non-oncolytic applications, the genes encoding ICP27, ICP0 and ICP4 are deleted (with or without additional deletion/inactivation of ICP22 and/or ICP47), or ICP27 and ICP4 deleted with an inactivating mutation in vmw65, or ICP4 deleted, again with an inactivating mutation in vmw65. Examples of such viruses include viruses reported by Samaniego et al 1998, Krisky et al 1998, or Thomas et al 1999.

Neurotrophic Virus Strains

Neurotrophic viruses, and particularly herpes simplex viruses such as HSV1 and HSV2 may be used according to the invention in the delivery of heterologous genes to the nervous system.

Viruses according to this embodiment of the invention typically have greater ability than a reference laboratory strain with equivalent modifications to infect a neuron, spread between cells in nervous tissue or to be transported within an axon. Capacity to infect neurons can be determined as set above as for cells in general. Ability to be transported within an axon or to spread between cells in nervous tissue can be determined by measuring the infection of cells in the nervous system at sites connected to the site of the original infection. Results may be analysed statistically as described above.

In these embodiments, it is preferred that, in an HSV strain, the virus is modified such that it lacks one, two, three or all of a functional ICP27-encoding gene, a functional ICP4-encoding gene, a functional ICP0-encoding gene, or a functional ICP22-encoding gene; or, in an non-HSV strain, the virus lacks a functional gene equivalent to one of said HSV genes; and/or, in an HSV strain, the virus lacks a functional vmw65 gene due to a mutation in said gene which abolishes its transcriptional-activation activity; or in a non-HSV strain, the virus lacks a functional gene equivalent to vmw65 due to a mutation in said gene which abolishes its transcriptional-activation activity.

Preferably, two or more of the genes encoding ICP27, ICP4, ICP0 and ICP22 are rendered non-functional, more preferably three and, still more preferably all four. Preferably, according to these embodiments a virus of the invention lacks both a functional gene encoding ICP4 and a functional gene encoding ICP27 and which has an inactivating mutation in the gene encoding vmw65 abolishing its transcriptional activation activity.

Such viruses may be used for the treatment of either peripheral nervous system disorders or central nervous system disorders. In the context of central nervous system disorders, it is particularly preferred that at least two immediate early genes selected from ICP0, ICP4, ICP22 and ICP27 are rendered non-functional.

Immunotherapeutic Viruses

In immunotherapeutic applications, herpes viruses of the invention are used to infect dendritic cells or other cells of the immune system, for example macrophages. Normally, herpes virus infection of dendritic cells reduces the capacity of the dendritic cells to stimulate an immune response. Accordingly, viruses of the invention are modified so that they are capable of efficiently infecting dendritic cells without preventing the dendritic cells from stimulating the immune system (WO00/08191). In such applications, the virus of the invention typically comprises a heterologous gene(s)which encodes an antigen gene product. This may be an antigen associated with a pathogenic infection or cancer. The gene is expressed in the dendritic cell and the gene produce presented as an antigen on the dendritic cell's surface. This stimulates an immune response to the antigen by activating T cells, which seek out cells displaying that antigen on their surface, i.e. tumours or pathogen cells or cells infected with a pathogen and destroy them.

Preferably, in an HSV strain, said virus lacks a functional UL43 gene, and/or a functional vhs gene, or, in a non-HSV strain, lacks a functional equivalent of UL43 and/or vhs; and optionally, in an HSV strain, lacks a functional vmw65 gene due to a mutation in said gene which abolishes its transcriptional-activation activity, or, in a non-HSV strain, lacks a functional gene equivalent to vmw65 due to a mutation in said gene which abolishes its transcriptional-activation activity; and optionally lacks at least one functional immediate early gene selected from ICP0, ICP4, ICP22 and ICP27.

In this context, it is preferred that a virus of the invention has greater ability than a reference laboratory strain with equivalent modifications to infect a dendritic cell or to stimulate an immune response. Infection of dendritic cells can be assessed as described above for cells in general. In particular, a non-laboratory virus strain of the invention will typically infect a greater percentage of dendritic cells than the reference laboratory strain when the dose of the two strains is the same. Statistical analysis can be conducted by the methods described above.

B. Complementing Cell Lines

When the virus of the invention is a herpes simplex virus which lacks a particular functional essential gene, for example a gene encoding ICP4 or ICP27, the virus of the invention is propagated on a cell line expressing that essential gene. For example, when the virus lacks a functional ICP27 gene, the virus may be propagated on V27 cells (Rice and Knipe, 1990), 2—2 cells (Smith et al, 1992) or B130/2 cells (Howard et al, 1998). When the virus lacks a functional ICP4 gene the virus may be propagated on a cell line expressing ICP4, for example E5 cells (DeLuca et al, 1985). When the virus lacks a functional ICP4 gene and a functional ICP27 gene the virus is propagated on a cell line expressing both ICP4 and ICP27 (such as E26 cells; Samaniego et al, 1995), and when the virus additionally lacks a functional vmw65 gene the virus may be propagated on a cell line also containing a non-HSV homologue of vmw65 (e.g. from equine herpes virus as in Thomas et al, 1999). Mutations to vmw65 may also be partially compensated for by inclusion of hexamethylene bisacetamide (HMBA) in the media used for virus growth (MacFarlane et al, 1992).

ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of ICP27– HSV strains, using methods known to those skilled in the art (for example, as described in Rice and Knipe, 1990).

Cell lines which do not allow reversion of an ICP27– mutant HSV strain to a strain with functional ICP27 are produced as described above, ensuring that the vector comprising a functional ICP27 gene does not contain sequences that overlap with (i.e. are homologous to) sequences remaining in the ICP27– mutant virus.

Where HSV strains of the invention comprise inactivating modifications in other essential genes, for example ICP4, complementing cell lines will comprise a functional HSV gene which complements the modified essential gene in the same manner as described for ICP27. For example, in the case of HSV strains comprising mutations in both ICP27 and ICP4, a cell line expressing both ICP27 and ICP4 is used (such as described in Samaniego et al, 1995 or in Thomas et al, 1999). HSV strains expressing other essential genes can be constructed in a similar manner to that described for ICP27. Here again, if it is ensured there is no sequence overlap between the remaining virus DNA and that inserted into the cell line for virus growth, the possibility of reversion of the virus to a less disabled form during growth will be minimised.

C. Methods of Mutation

The various viral genes referred to may be rendered functionally inactive by several techniques well known in the art. For example, they may be rendered functionally inactive by deletion(s), substitution(s) or insertion(s), preferably by deletion. A deletion may remove a portion of the genes or the entire gene. For example, deletion of only one nucleotide may be made, resulting in a frame shift. However, preferably a larger deletion is made, for example at least 25%, more preferably at least 50% of the total coding and non-coding sequence (or alternatively, in absolute terms, at least 10 nucleotides, more preferably at least 100 nucleotides, most preferably at least 1000 nucleotides). It is particularly preferred to remove the entire gene and some of the flanking sequences. An inserted sequence may include one or more of the heterologous genes described below. In the case of the vmw65 gene, the entire gene is not deleted since it encodes an essential structural protein, but a small inactivating mutation is made which abolishes the ability of vmw65 to activate transcriptionally IE genes (e.g. as in Ace et al, 1989 or Smiley et al, 1997).

Mutations are made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise a deletion(s), insertion(s) or substitution(s), all of which may be constructed by routine techniques. Insertions may include selectable marker genes, for example lacZ or GFP, for screening recombinant viruses by, for example β-galactosidase activity or fluorescence.

D. Heterologous Genes and Promoters

The viruses of the invention may be modified to carry a heterologous gene/genes. The term "heterologous gene" encompasses any gene. Although a heterologous gene is typically a gene not present in the genome of a herpes virus, herpes gene/genes may be used provided that the coding sequence is not operably linked to the viral control sequences with which it is naturally associated. The heterologous gene may be any allelic variant of a wild-type gene, or it may be a mutant gene. The term "gene" is intended to cover nucleic acid sequences which are capable of being at least transcribed. Thus, sequences encoding mRNA, tRNA and rRNA are included within this definition. However, the present invention is concerned with the expression of polypeptides rather than tRNA and rRNA. Sequences encoding mRNA will optionally include some or all of 5' andor 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements.

The heterologous gene/genes may be inserted into the viral genome by homologous recombination of HSV strains with, for example plasmid vectors carrying the heterologous gene/genes flanked by HSV sequences. The heterologous gene/genes may be introduced into a suitable plasmid vector comprising herpes viral sequences using cloning techniques well-known in the art. The heterologous gene/genes may be inserted into the viral genome at any location provided that the virus can still be propagated. It is preferred that the heterologous gene/genes is inserted into an essential gene. Heterologous genes may be inserted at multiple sites within the virus genome.

The transcribed sequence of the heterologous gene/genes is preferably operably linked to a control sequence permitting expression of the heterologous gene/genes in mammalian cells, preferably a tumour cell or a cell of the nervous system. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene/genes and a signal for termination of transcription. The promoter is selected from promoters which are functional in mammalian, preferably human, cells of the nervous system or in tumours or in cells of the immune system. The promoter/promoters may be derived from promoter sequences of eukaryotic genes. For example, promoters may be derived from the genome of a cell in which expression of the heterologous gene is to occur, preferably a mammalian, preferably human cell. With respect to eukaryotic promoters, they may be promoters that function in a ubiquitous manner (such as promoters of β-actin, tubulin) or, alternatively, a tissue-specific manner, such as the neuron-specific enolase (NSE) promoter. They may also be promoters that respond to specific stimuli, for example promoters that bind steroid hormone receptors. Viral promoters may also be used, for example the Moloney murine leukaemia virus long terminal repeat (MMLV) LTR promoter or other retroviral promoters, the human or mouse cytomegalovirus (CMV) IE promoter, or promoters of herpes virus genes including those driving expression of the latency associated transcripts.

Expression cassettes and other suitable constructs comprising the heterologous gene/genes and control sequences can be made using routine cloning techniques known to persons skilled in the art (see, for example Sambrook et al, 1989, Molecular Cloning—A laboratory manual: Cold Spring Harbor Press).

It may also be advantageous for the promoters to be inducible so that the levels of expression of the heterologous gene can be regulated during the life-time of the cell. Inducible means that the levels of expression obtained using the promoter can be regulated. For example, in a preferred embodiment where more than one heterologous gene is inserted into the HSV genome, one promoter would comprise a promoter responsive to the tet repressor/VP16 transcriptional activator fusion protein previously reported (Gossen and Bujard, 1992, Grossen et al, 1995), and driving the heterologous gene the expression of which is to be regulated. The second promoter would comprise a strong promoter (e.g. the CMV IE promoter) driving the expression of the tet repressor/VP16 fusion protein. Thus, in this example, expression of the first heterologous gene would depend on the presence or absence of tetracycline.

Heterologous genes will typically encode polypeptides of therapeutic use. For example, in the nervous system in non-oncolytic applications, genes which may modulate pain, stimulate nerve re-growth or prevent nerve degeneration. In oncolytic applications, heterologous genes may encode proteins which are themselves cytotoxic, encode pro-drug activating enzymes or which are capable of stimulating or enhancing an anti-tumour immune response.

Heterologous genes may also include marker genes (for example, encoding β-galactosidase or green fluorescent protein or other fluorescent proteins) or genes whose products regulate the expression of other genes (for example, transcriptional regulatory factors including the tet repressor/vmw65 transcriptional activator fusion protein described above).

Gene therapy and other therapeutic applications may well require the administration of multiple genes. The expression of multiple genes may be advantageous for the treatment of a variety of conditions. Herpes viruses are uniquely appropriate as they do not have the limited packaging capabilities of other viral vector systems. Thus, multiple heterologous genes can be accommodated within its genome. For example, from 2 to 5 genes may be inserted into the genome.

There are, for example, at least two ways in which this could be achieved. For example, more than one heterologous gene and associated control sequences could be introduced into a particular HSV strain either at a single site or at multiple sites in the virus genome. It would also be possible to use pairs of promoters (the same or different promoters) facing in opposite orientations away from each other, these promoters each driving the expression of a heterologous gene (the same or different heterologous gene) as described above.

E. Therapeutic Uses

Viruses of the invention may be used in methods of therapy. In particular, oncolytic viruses of the invention may be used in applications including the oncolytic treatment of cancer, e.g. by direct intra-tumour injection. Where the virus comprises a heterologous gene encoding a prodrug activator, additional pro-drug therapy may be carried out. Additionally, treatment may be combined with or stimulation of an immune response by any means known in the art. Viruses of the invention may be used in the therapeutic treatment of any solid tumour in a mammal, preferably in a human. For example viruses of the invention may be administered to a subject with prostate, breast, lung, liver, endometrial, bladder, colon or cervical carcinoma; adenocarcinoma; melanoma; lymphoma; glioma; or sarcomas such as soft tissue and bone sarcomas.

Replication incompetent viruses of the invention may be used in the delivery of genes to individuals requiring gene therapy. In particular, neurotrophic viruses of the invention may be used in the treatment of disorders of the central or peripheral nervous system. Preferred central nervous system disorders for treatment or prevention include neurodegenerative disorders. Particularly preferred central nervous system disorders for treatment or prevention are stroke, Parkinson's disease, Alzheimer's disease, Tay Sachs disease and mucopolysaccaride diseases. Preferred peripheral nervous system disorders for treatment or prevention include motor neuron disease, chronic pain and peripheral nerve damage.

Immunotherapeutic viruses of the invention may be used in the prevention or treatment of the pathogenic infection or cancer with which the antigen their inserted heterologous coding gene is associated.

F. Administration

The viruses of the invention may thus be used in a patient, preferably a human patient, in need of treatment. Viruses of the invention may be used for the oncolytic treatment of cancer, and herpes viruses of the invention (in addition to oncolytic applications) for the treatment of, for example pain, degenerative conditions of the nervous system, or to stimulate nerve re-growth. The aim of therapeutic treatment is to improve the condition of the patient. Typically therapeutic treatment using a virus of the invention will allieviate the symptoms of the disease or condition of the patient being treated. A method of treatment according to the invention therefore comprises administering a therapeutically effective amount of a virus of the invention to a patient suffering from cancer, pain, a neurodegenerative condition or nerve damage.

Administration of an oncolytic virus of the invention to a patient suffering from a tumour will typically kill the cells of the tumour thus decreasing the size of the tumour and/or preventing the spread of malignant cells from the tumour. Administration of a virus of the invention to a patient suffering from other diseases such as pain, degenerative conditions or nerve damage will typically improve the condition of the patient. For example by lessening the severity of the pain, slowing the degeneration of nervous tissue or promoting nerve regrowth.

One method of administering therapy involves combining the virus with a pharmaceutically acceptable carrier or diluent to produce a pharmaceutical composition. Suitable carriers and diluents include isotonic saline solutions, for example phosphate-buffered saline.

Oncolytic treatment and/or gene delivery to cells for therapeutic purposes may then be carried out following direct injection of the vector composition into target tissue. The amount of virus administered is in the case of HSV in the range of from $10^4$ to $10^{10}$ pfu, preferably from $10^5$ to $10^8$ pfu, more preferably about $10^6$ to $10^8$ pfu. When injected for oncolytic or non-oncolytic treatment, typically up to 500 µl, typically from 1–200 µl, preferably from 1–10 µl of a pharmaceutical composition consisting esentially of the virus and a pharmaceutically acceptable suitable carrier or diluent, would be used for injection. However, for some oncolytic therapy applications larger volumes up to 10 ml may also be used, depending on the tumour and inoculation site.

The routes of administration and dosages described are intended only as a guide since a skilled practitioner will be able to determine readily the optimum route of administration and dosage. The dosage may be determined according to various parameters, especially according to the age, weight and condition of the patient to be treated, the severity of the disease or condition and the route of administration.

The preferred route of administration to a patient suffering from cancer is by direct injection into the tumour. The virus may also be administered systemically or by injection into a blood vessel supplying the tumour. The optimum route of administration will depend on the location and size of the tumour. The dosage may be determined according to various parameters, especially according to the location of the tumour, the size of the tumour, the age, weight and condition of the patient to be treated and the route of administration.

G. Non-Therapeutic Aspects

Also provided are methods of identifying suitable clinical strains for modification according to the invention. In addition, methods of target validation are provided. These concern the identification of genes suitable for use in the therapeutic applications of the invention as described above.

Methods of production of viruses of the invention are also provided.

The Following Examples Illustrate the Invention.

Herpes simplex type-1 virus (HSV1) in which the neurovirulence factor ICP34.5 is inactivated has previously been shown to direct tumour specific cell lysis in tumour models both in vitro and in vivo. Such viruses have also been shown to be safe in Phase I clinical trials by direct intracerebral injection in late stage glioma patients.

Previous work has used serially passaged laboratory isolates of HSV1 (viruses derived from HSV1 strain 17+ or HSV1 strain F) which might be anticipated to be attenuated in their lytic capability in human tumour cells as compared to more recent clinical isolates.

In work aimed at producing ICP34.5 deleted HSV with enhanced oncolytic and anti-tumour potential, we have deleted ICP34.5 from an HSV1 clinical isolate and compared replicative and lytic potential in a number of human tumour cell types in comparison to HSV1 strain 17+ (a standard laboratory strain).

Virus Construction (See FIG. 1)

The viruses used were either based on HSV1 strain 17+ (a standard laboratory strain) or two clinical isolates derived from cold sores from frequent re-activators of HSV1. These strains were named BL1 and JS1. ICP34.5 was completely deleted from strain 17+ and JS1 together with the insertion of a CMV-GFP cassette. JS1 was also further engineered by the insertion of human or mouse GM-CSF so as to replace the ICP34.5 gene. BL1 and JS1 are thus clinical isolates, or "non-laboratory" strains. The derivatives of JS1 discussed herein are also non-laboratory strains, i.e. modified non-laboratory strains of the invention.

Figure 2:
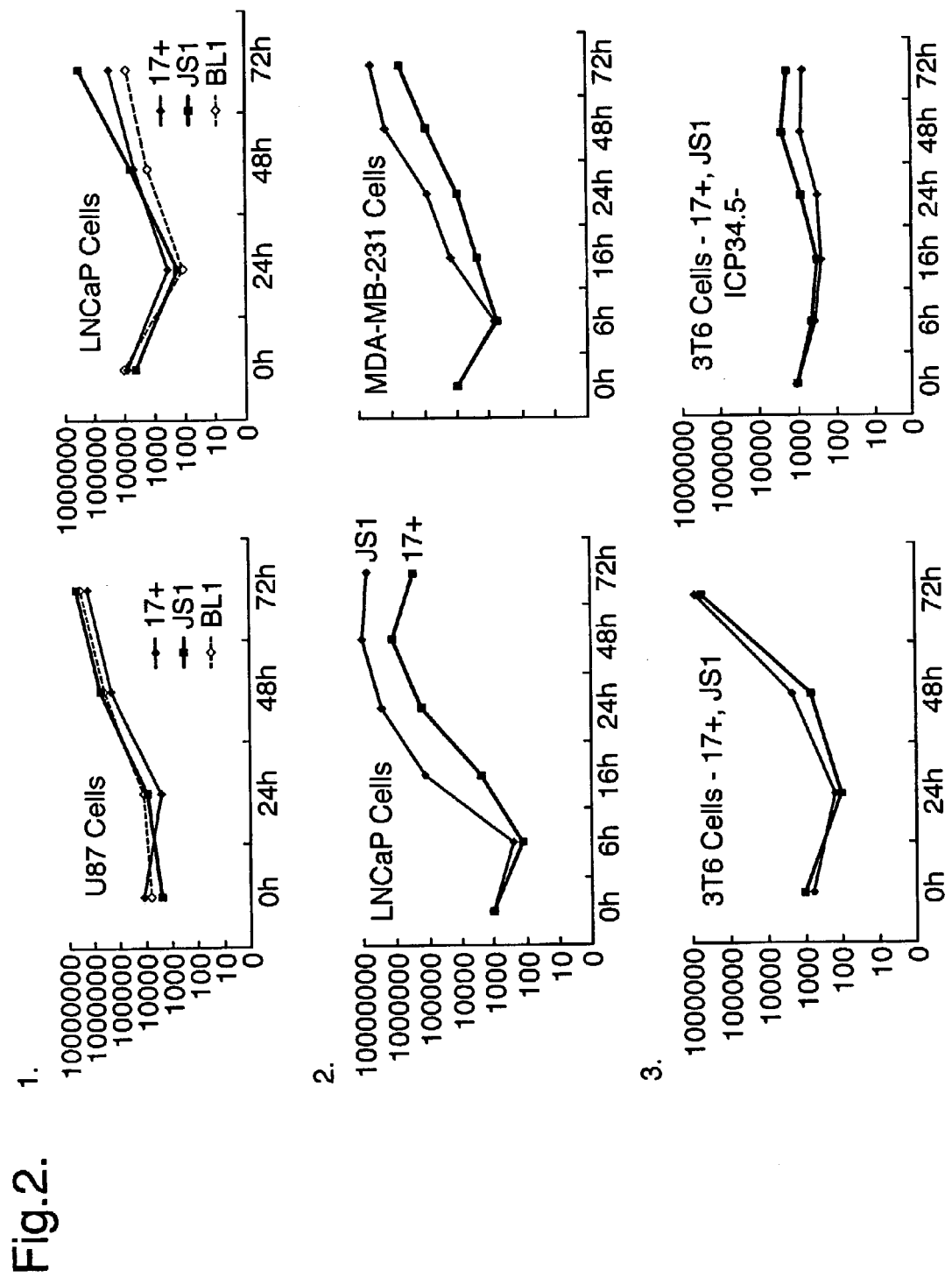
FIG. 2. Clinical isolates show enhanced growth in tumour cells
(1) Growth of 17+, BL1 and JS1. Left hand diagram: U87 cells. Right-hand diagram: LNCaP cells.
(2) Growth of ICP34.5− 17+ and JS1 on tumour cells. Left-hand diagram: LNCaP cells. Right-hand diagram: MDA-MB-231 cells.
(3) JS1/34.5− does not grow on cells non-permissive for HSV ICP34.5 mutants. Left-hand diagram: 3T6 cells—17+, JS1. Right-hand diagram: 3T6 cells—17+, JS1 ICP34.5−.

Virus Growth in Tumour Cells (See FIG. 2)

JS1 and BL1 showed enhanced growth in some human tumour cells tested as compared to HSV1 ICP34.5 deleted strain 17+ when tested over a 72 hour period (FIG. 2). JS1 was selected for further study and the modifications described above (see FIG. 1, and above) were made to it.

Figure 3:
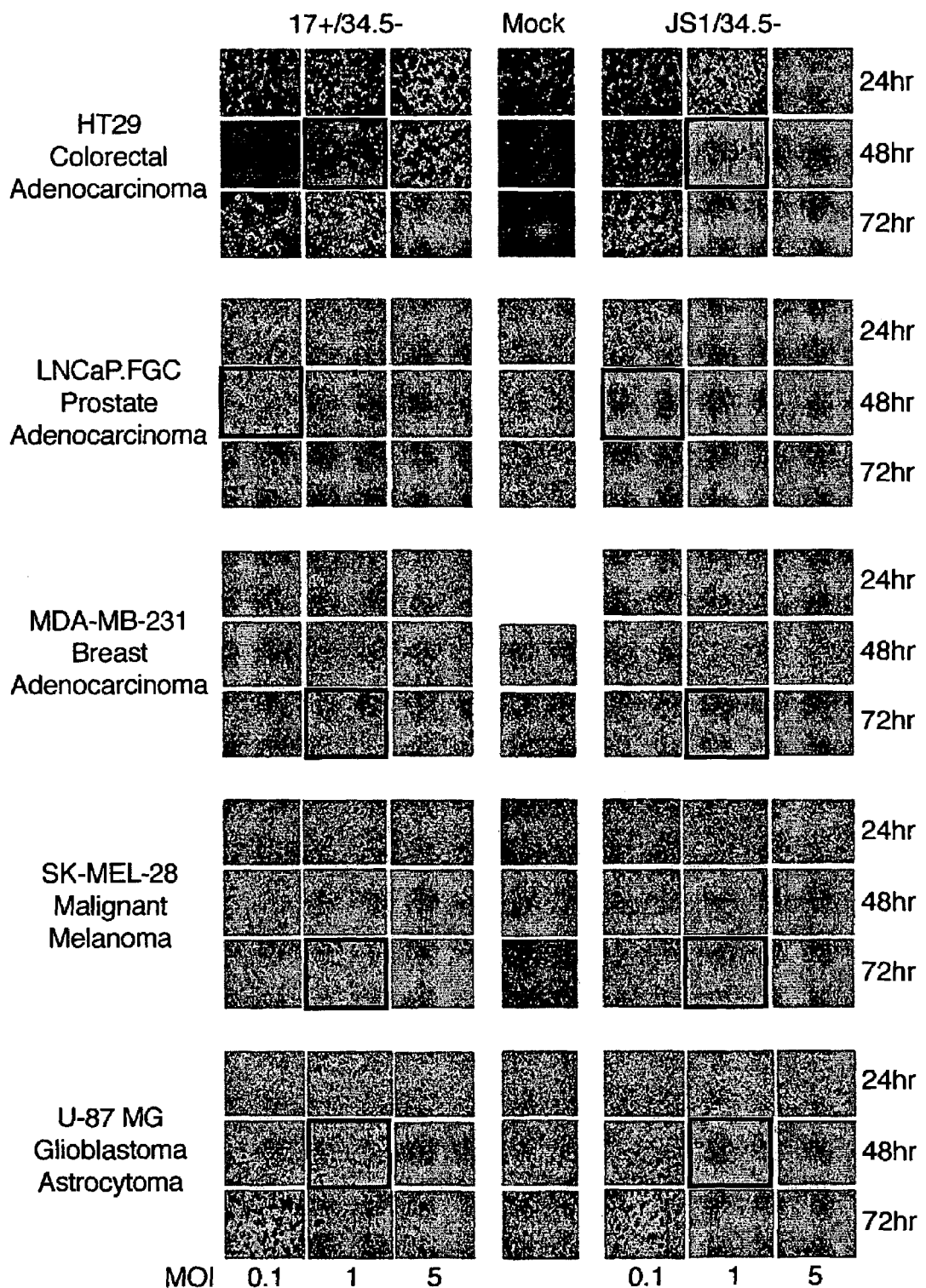
FIG. 3. An ICP34.5 deleted HSV clinical isolate shows enhanced lysis in all tumour cells tested
Tumour cell lines were either mock infected, infected with HSV1 strain 17+/34.5−, or infected with HSV1 strain JS3/34.5− at the indicated MOI and stained with crystal violet at time points after infection to allow visualisation of cells. Each block of photographs relates to a cell type. From top to bottom, these are HT29 colorectal adenocarcinoma, LNCaP.FGC prostate adenocarcinoma, MDA-MB-231 breast adenocarcinoma, SK-MEL-28 malignant melanoma and U-87 MG glioblastoma astrocytoma. Left-hand blocks relate to results for HSV1 strain 17+/34.5−. Right-hand blocks relate to results for HSV1 strain JS1/34.5−. Central blocks represent mock infected cells. Within each block, the top row represents a 24 hour time-point, the second a 48 hour time-point and the third a 72 hour time-point within each block, the left-hand column represents MOI=0.2, the central column MOI=0.1 and the right-hand column MOI=5.

Lytic Capabilities of Viruses (See FIG. 3)

Lytic (cell killing) capabilities were enhanced with the JS1-derived non-laboratory strains derived virus in all tumour cell lines tested. More particularly, with reference to FIG. 3, the JS1/34.5– virus, i.e. JS1 with ICP34.5 removed by deletion, showed enhanced lytic capabilities in HT29 colorectal adenocarcinoma, LNCaP.FGC prostate adenocarcinoma, MDA-MB-231 breast adenocarcinoma, SK-MEL-28 malignant melanoma and U-87 MG glioblastoma astrocytoma cells.

Lytic capabilities were also assessed in SK-MEL-28, MDA-MB-231 and HT29 cells by trypan blue exclusion assay of infected cells at various doses and times after infection with BL1, JS1 as compared to strain 17+. Trypan blue is excluded from live cells and so numbers of live cells remaining in a culture can be assessed by this means. Tumour cell lines cultured in duplicate wells of six well dishes were infected for 24, 48 or 72 hrs at an MOI of 0.1 or 1 with either 17+, BL1 or JS1 and numbers of live cells were counted. The percentage of the number of live cells in equivalent uninfected control wells are shown in Table 1.

Thus, as in all cases more tumour cells are killed with the clinical isolate viruses BL1 and JS1 than the laboratory isolate 17+, to provide increased oncolytic activity, the use of recent clinical virus strains is likely to enhance the anti-tumour capabilities of such viruses modified to give tumour selective replication (e.g. by the deletion of ICP34.5) when used in human patients for cancer treatment.

TABLE 1

| | | JS1 | | 17 | | BL1 | |
|---|---|---|---|---|---|---|---|
| | | percentage of number of live cells in uninfected control wells | | | | | |
| Cell line | time after infection | MOI = 0.1 | MOI = 1 | MOI = 0.1 | MOI = 1 | MOI = 0.1 | MOI = 1 |
| SK-MEL-28 | 24 h | 41 | 8 | 57.3 | 19 | 43.7 | 6.67 |
| | duplicate samples | 33.7 | 7 | 62.6 | 19.3 | 39 | 6.33 |
| | 48 h | 5.51 | 1.9 | 7.4 | 3.7 | 4.5 | 0.8 |
| | | 5.05 | 0.8 | 7.1 | 2.6 | 4.8 | 1.1 |
| | 72 h | 0 | 0 | 0 | 0 | 0 | 0 |
| | | 0 | 0 | 0 | 0 | 0 | 0 |
| MDA-MB-231 | 24 h | 44.91 | 16.7 | 69.37 | 36.34 | 55.63 | 26.79 |
| | | 44.02 | 16.96 | 65.8 | 34.55 | 60.45 | 25.27 |
| | 48 h | 14.1 | 4.7 | 27.9 | 8.3 | 18 | 6.7 |
| | | 13.5 | 3.8 | 27 | 8.5 | 20 | 8.3 |
| | 72 h | 0 | 0 | 2.91 | 0.73 | 1.46 | 0 |
| | | 0 | 0 | 2.91 | 1.27 | 1.64 | 0 |
| HT-29 | 24 h | 37.53 | 15 | 47.28 | 23.61 | 42.22 | 22.15 |
| | | 39.24 | 15 | 45.76 | 24.24 | 43.04 | 21.33 |
| | 48 h | 13.2 | 2.3 | 29.4 | 4.2 | 18.4 | 4.4 |
| | | 14 | 3 | 27.7 | 4.7 | 21.2 | 3.7 |
| | 72 h | 0 | 0 | 1.57 | 0 | 1.64 | 0 |
| | | 0 | 0 | 1.89 | 0 | 1.57 | 0 |

Further Enhanced Anti-Tumour Activity

Further enhanced activity may also be anticipated if these viruses are then used to deliver genes with anti-tumour activity. Such genes include those encoding pro-drug activators or immune stimulatory proteins.

For this purpose, we have produced from JS1 an ICP34.5 deleted clinical isolated of HSV1 which expresses human or mouse GM-CSF GM-CSF is a potent immune stimulator. This virus is designed to enhance anti-tumour immune responses following intra-tumoral injection.

REFERENCES

Chou et al, 1990, Science 250: 1262–1266
Maclean et al, 1991, J. Gen. Virol. 72: 631–639
Samaniego et al, 1998, J. Virol. 72: 3307–3320
Krisky et al, 1998, Gene Therapy 5: 1593–1603
Thomas et al, 1999, J. Virol. 73: 7399–7409
MacFarlane et al, 1992, J. Gen. Virol. 73: 285–292
Howard et al, 1998, Gene Therapy 5: 1137–1147
Samaniego L A et al, 1995, J. Virol. 69: 5705–5715
Ace C I et al, 1989, J. Virol. 63: 2260–2269
Smith I L et al, 1992, Virol. 186: 74–86
Rice, S A and Knipe D M, 1990, J. Virol. 64: 1704–1715
DeLuca N A et al, 1985, J. Virol. 56: 558–570
Gossen M & Bujard H, 1992, PNAS 89: 5547–5551
Gossen M et al, 1995, Science 268: 1766–1769
Smiley, J. R. & Duncan J., 1997, J. Virol. 71: 6191–6193
Thompson et al 1998, Virus Genes 1(3); 275–286
Meignier et al 1998, J. Infect. Dis. 159; 602–614

DEPOSIT INFORMATION

HSV1 Strain JS1 has been deposited at the European Collection of Cell Cultures (ECACC), CAMR, Salisbury, Wiltshire SP4 0JG, United Kingdom, on Jan. 2, 2001 under accession number 01010209.

The invention claimed is:

1. A method of treating a tumor in an individual in need thereof, comprising the step of administering to said individual an effective amount of an oncolytic herpes simplex virus 1 strain (HSV1), wherein said oncolytic (HSV1) strain is a clinical isolate from a recurrent cold sore modified such that it lacks a function ICP34.5-encoding gene, wherein said modified clinical isolate has a greater ability than a reference laboratory HSV strain modified in the same manner as the clinical isolate to replicate in or kill tumor cells, and wherein said reference laboratory strain is selected from the group consisting of HSV1 strain 17+, HSV1 strain F and HSV1 strain KOS.

2. The method of claim 1, wherein said clinical isolate has undergone 100 or less cycles of serial passage since isolation from its host.

3. The method of claim 1, wherein said HSV1 strain is further modified such that it lacks one or more of, a functional ICP6-encoding gene or a functional thymidine kinase-encoding gene.

4. The method of claim 1, wherein the HSV1 further lacks a functional ICP47 gene.

5. A method according to claim 1 wherein said HSV1 further comprises a heterologous gene.

6. A method according to claim 5 wherein said heterologous gene is a gene capable of modifying immune responses.

7. A method according to claim 6 wherein said heterologous gene capable of modifying immune responses encodes an immune stimulatory polypeptide or another gene product capable of modifying immune responses, a prodrug activator, a tumour suppressor or a pro-apoptotic gene product.

8. A method according to claim 7 wherein said immune stimulatory polypeptide is granulocyte macrophage colony-stimulating factor (GMCSF), another cytokine or chemokine, RANTES, B7.1 or B7.2 or IL12, or wherein the prodrug activator is nitroeductase or cytochrome p450, or wherein the tumour suppressor is p53.

9. The method of claim 2, wherein said clinical isolate HSV1 has undergone 50 or less cycles of serial passage since isolation from its host.

10. The method of claim 9, wherein said clinical isolate HSV1 has undergone 20 or less cycles of serial passage since isolation from its host.

11. The method of claim 10, wherein said clinical isolate HSV1 has undergone 10 or less cycles of serial passage since isolation from its host.

12. The method of claim 1, wherein said clinical isolate HSV1 has undergone one year or less in culture since isolation from its host.

13. The method of claim 12, wherein said clinical isolate HSV1 has undergone six months or less in culture since isolation from its host.

14. The method of claim 13, wherein said clinical isolate HSV1 has undergone one month or less in culture since isolation from its host.

15. The method of claim 1, wherein said clinical isolate is a HSV1 JS1 strain, HSV1 JS1 being deposited at the European Collection of Cell Cultures (ECACC) under accession number 01010209.

16. The method of claim 1, wherein said individual is human.

* * * * *